US 10,918,267 B2

(12) United States Patent
Sato et al.

(10) Patent No.: US 10,918,267 B2
(45) Date of Patent: Feb. 16, 2021

(54) ENDOSCOPE

(71) Applicant: OLYMPUS CORPORATION, Tokyo (JP)

(72) Inventors: Eijiro Sato, Hachioji (JP); Chikayoshi Meguro, Hachioji (JP); Kenji Takatsuji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 341 days.

(21) Appl. No.: 16/101,562

(22) Filed: Aug. 13, 2018

(65) Prior Publication Data

US 2018/0360296 A1 Dec. 20, 2018

Related U.S. Application Data

(63) Continuation of application No. PCT/JP2016/080504, filed on Oct. 14, 2016.

(30) Foreign Application Priority Data

Feb. 18, 2016 (JP) .............................. JP2016-028823

(51) Int. Cl.
*A61B 1/00* (2006.01)
*A61B 1/005* (2006.01)
(Continued)

(52) U.S. Cl.
CPC .......... *A61B 1/0052* (2013.01); *A61B 1/0057* (2013.01); *A61B 1/00066* (2013.01); *G02B 23/2476* (2013.01); *A61B 1/307* (2013.01)

(58) Field of Classification Search
None
See application file for complete search history.

(56) References Cited

U.S. PATENT DOCUMENTS 4,616,630 A 10/1986 Arakawa
5,836,894 A * 11/1998 Sarvazyan ........... A61B 1/0052
600/587

(Continued)

FOREIGN PATENT DOCUMENTS

EP 2617344 A1 7/2013
EP 3050488 A1 8/2016
(Continued)

OTHER PUBLICATIONS

International Search Report dated Dec. 13, 2016 issued in PCT/JP2016/080504.

*Primary Examiner* — Timothy J Neal
(74) *Attorney, Agent, or Firm* — Scully, Scott, Murphy & Presser, P.C.

(57) ABSTRACT

An endoscope includes: an insertion portion including a bending portion; an operation portion including a grasping portion and an operation portion main body; a pedestal portion protruded from the operation portion main body; a shaft member configured to be tilted; a finger contact portion on which a finger of a hand is placed, the finger contact portion being provided at an end portion of the shaft member; and a step portion on which a finger of the operator's hand, which is different from the finger placed on the finger placing portion, is placed, the step portion being provided at a position which is outside of a peripheral edge of the pedestal portion and which is an opposite side of the grasping portion across the shaft member.

7 Claims, 10 Drawing Sheets

(51) Int. Cl.
    *G02B 23/24*  (2006.01)
    *A61B 1/307*  (2006.01)

(56) References Cited

U.S. PATENT DOCUMENTS

| | | |
|---|---|---|
| 2013/0060088 A1 | 3/2013 | Okamoto |
| 2016/0242629 A1 | 8/2016 | Hijihara et al. |

FOREIGN PATENT DOCUMENTS

| | | |
|---|---|---|
| JP | S61-039503 U1 | 3/1986 |
| JP | 2009-189685 A | 8/2009 |
| JP | 2010-259609 A | 11/2010 |
| JP | 2013-158571 A | 8/2013 |
| JP | 2014-102625 A | 6/2014 |
| WO | WO 2012/117865 A1 | 9/2012 |
| WO | WO 2015/141039 A1 | 9/2015 |

\* cited by examiner

ENDOSCOPE

CROSS REFERENCE TO RELATED APPLICATION

This application is a continuation application of PCT/JP2016/080504 filed on Oct. 14, 2016 and claims benefit of Japanese Application No. 2016-028823 filed in Japan on Feb. 18, 2016, the entire contents of which are incorporated herein by this reference.

BACKGROUND OF THE INVENTION

1. Field of the Invention

The present invention relates to an endoscope including, at an operation portion thereof, a bending operation lever configured to be tilted when a bending portion is bent.

2. Description of the Related Art

Endoscopes include an elongated insertion portion and an observation optical system provided on a distal end side of the insertion portion. Some endoscopes include, on the distal end side of the insertion portion thereof, a bending portion configured to bend in two directions, i.e., up and down directions or in four directions, i.e., up, down, left, and right directions. Such endoscopes are provided with the bending portion at the insertion portion, thereby capable of improving the insertion performance when being inserted into a subject and capable of performing a wide-range observation by changing the field-of-view direction.

Generally, an operation portion configured to serve also as a grasping portion is provided at the proximal end portion of the insertion portion. The endoscopes provided with a bending portion include, at the operation portion, a bending operation device for performing bending operation of the bending portion. The bending operation device is provided at an operation portion main body of the operation portion so as to be operable with the hand and fingers of an operator, such as a doctor, grasping the grasping portion.

The bending operation device includes a bending operation knob of a substantially circular shape which is rotatably attached to the operation portion main body with a shaft member, and a substantially L-shaped operation lever disclosed in Japanese Patent Application Laid-Open Publication No. 2009-189685, or an operation element which stands upright at the operation portion and configured to be tiltable, as disclosed in Japanese Patent Application Laid-Open Publication No. 2013-158571.

The bending portion is configured to bend by pulling or relaxing the bending wires by the operator rotating the bending operation knob or the operation lever around the shaft member. The endoscope including the bending portion configured to bend in four directions includes a pair of bending operation knobs or a pair of operation levers at the operation portion.

In contrast, one end portion of the operation element configured to be tilted protrudes outward from one surface of the operation portion main body so as to be tiltable. The other end portion of the operation element is fixed to, for example, a cross-shaped suspended frame with arm portions which is provided in the operation portion.

In the endoscope including the operation element, the bending wires are pulled and relaxed by the operator tilting the operation element in a desired direction at a desired angle, which causes the bending portion to bend by a desired amount.

Thus, the operation element configured to be tiltable is preferable for intuitively bending the bending portion provided at the insertion portion of the endoscope and configured to bend in four directions.

Note that the endoscope disclosed in the Japanese Patent Application Laid-Open Publication No. 2013-158571 includes a power-assisted bending drive mechanism configured to pull the bending wires by the rotation driving force generated by a motor in conjunction with the tilting operation by the operator, to thereby assist the bending portion to bend.

On the other hand, the applicant of the present application discloses, in Japanese Patent Application No. 2014-102625, the endoscope which can realize equivalent operability by either of the left hand and right hand, without increasing the size of the operation portion.

SUMMARY OF THE INVENTION

An endoscope according to one aspect of the present invention includes: an insertion portion which includes a bending portion and into which bending wires corresponding to four directions of up, down, left, and right are inserted; an operation portion including a grasping portion provided on a proximal end side of the insertion portion and an operation portion main body; a pedestal portion provided in a protruded manner on the operation portion main body of the operation portion; a bending operation lever provided so as to protrude outward from an upper surface center of the pedestal portion, the bending operation lever being configured to be tilted by an operator with a finger of a hand grasping the grasping portion so as to pull at least one of the bending wires in a state where the operator grasps the grasping portion of the operation portion; a finger contact portion on which the finger of the operator's hand grasping the grasping portion is placed when the bending operation lever is tilted, the finger contact portion being provided at an end portion of the bending operation lever protruded outward; a side surface of the pedestal portion formed outside of a peripheral edge of the pedestal portion, the side surface being a surface rising from the operation portion main body; and a step portion on which a finger of the operator's hand grasping the grasping portion, which is different from the finger placed on the finger contact portion, is capable of being placed, the step portion including the side surface of the pedestal portion and being formed on an opposite side of the grasping portion grasped by the operator across the bending operation lever.

An endoscope according to another aspect of the present invention includes: an insertion portion which includes a bending portion and into which bending wires corresponding to four directions of up, down, left, and right are inserted; an operation portion provided on a proximal end side of the insertion portion, and including a first grasping portion having a first longitudinal axis parallel to a longitudinal axis of the insertion portion, a second grasping portion having a second longitudinal axis intersecting with the first longitudinal axis, and an operation portion main body formed in a flex shape and coupling the first grasping portion and the second grasping portion; a pedestal portion provided in a protruded manner on a flex-shaped outer side surface of a flex portion of the operation portion main body; a bending operation lever provided so as to protrude outward from an upper surface center of the pedestal portion, the bending operation lever being configured to be tilted by an operator with a finger of a hand grasping the grasping portion in a first grasping manner in which the operator grasps the first grasping portion or in a second grasping manner in which the operator grasps the second grasping portion, so as to pull at least one of the bending wires; a finger contact portion on which the finger of the operator's hand grasping the grasping portion is placed when the bending operation lever is tilted in the first grasping manner or the second grasping manner, the finger contact portion being provided at an end portion of the bending operation lever protruded outward; side surfaces of the pedestal portion formed outside of a peripheral edge of the pedestal portion, each of the side surfaces being a surface rising from the operation portion main body; a first grasping manner step portion on which a finger of the operator's hand, which is different from the finger placed on the finger contact portion, is capable of being placed in the first grasping manner, the first grasping manner step portion including one of the side surfaces of the pedestal portion and provided at a position on a side of the second grasping portion; and a second grasping manner step portion on which a finger of the operator's hand, which is different from the finger placed on the finger contact portion, is capable of being placed in the second grasping manner, the second grasping manner step portion including the other of the side surfaces of the pedestal portion and provided at a position on a side of the first grasping portion.

DETAILED DESCRIPTION OF THE PREFERRED EMBODIMENT(S)

Figure 1:
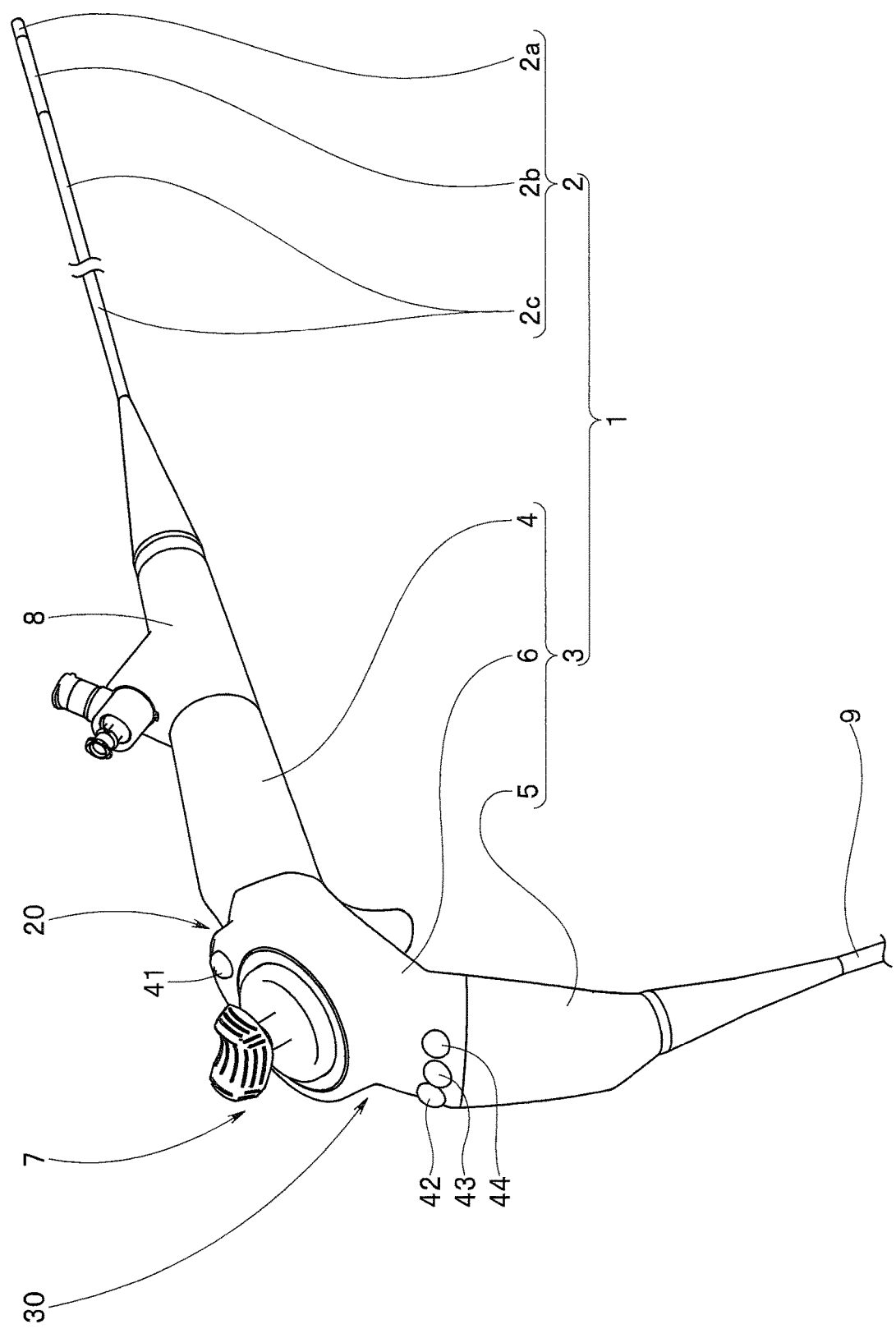
FIG. 1 describes an endoscope.

The present invention will be described with reference to the drawings.

Each of the drawings used in the description below schematically shows the components, and there is a case where a different dimensional relationship, a different scale size, etc., are used for each of the components in order to allow each of the components to be illustrated in a recognizable size in the drawings. Therefore, with regard to the number, shapes, ratio of the sizes of the components, and a relative positional relationship among the components, the present invention is not limited only to those shown in the drawings.

An endoscope 1 shown in FIG. 1 is an endoscope to be used in the urology department, for example.

The endoscope 1 includes an elongated insertion portion 2 configured to be inserted into a subject and an operation portion 3. The insertion portion 2 includes, in the following order from the distal end side, a distal end portion 2a, a bending portion 2b, and a flexible tube portion 2c that are provided in a linked manner. In the distal end portion 2a, an image pickup unit including an image pickup device such as CCD, CMOS, etc., is incorporated. The bending portion 2b is configured to bend in four directions, i.e., up, down, left, and right directions, for example. The flexible tube portion 2c has flexibility and configured to bend passively.

The operation portion 3 mainly includes a first grasping portion 4, a second grasping portion 5, and an operation portion main body 6. The first grasping portion 4, the second grasping portion 5, and the operation portion main body 6 are cylindrical members. The operation portion main body 6 includes, in the internal space thereof, a bending operation mechanism portion, and a bending operation device 7, which constitutes the bending operation mechanism portion, protrudes from the operation potion main body 6. A first step portion 20 and a second step portion 30, to be described later, are provided opposed to each other across the bending operation device 7.

The reference sign 8 denotes a port rotating portion and provided between the insertion portion 2 and the first grasping portion 4. Specifically, the distal end side of the port rotating portion 8 is connected to the insertion portion 2 through a break-prevention portion. On the other hand, the proximal end side of the port rotating portion 8 is rotatably coupled to the distal end side of the first grasping portion 4 through a rotating mechanism (not shown). The reference sign 8a denotes an opening part such as a treatment instrument insertion port and provided, in a protruded manner, on the outer circumferential surface of the port rotating portion 8.

The reference sign 9 denotes a universal cord. The universal cord 9 is extended from the proximal end side of the second grasping portion 5. The universal cord 9 includes, at an extension end thereof, an endoscope connector (not shown). The endoscope connector is connectable to a light source apparatus (not shown) as an external apparatus of the endoscope 1 or a signal processing apparatus for endoscope (not shown).

The reference signs 41, 42, 43, and 44 are various operation switches, and include, for example, an observation mode switching switch for instructing the switching of the observation mode, a freeze switch for generating a freeze signal, a release switch for generating a release signal when performing photographing, and the like.

Figure 2:
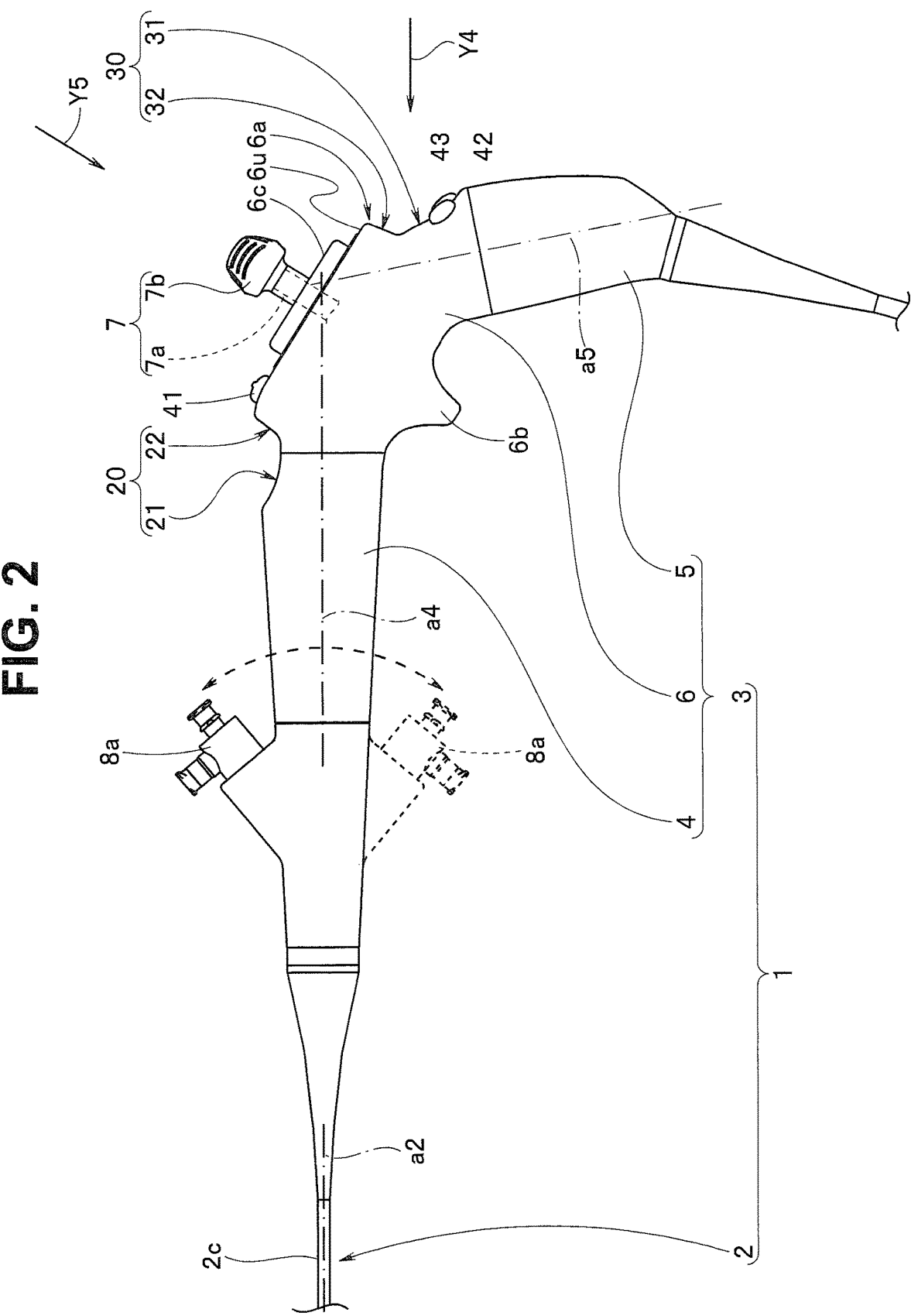
FIG. 2 is a side view describing the endoscope in FIG. 1.

As shown in FIG. 2, the operation portion main body 6 is a coupling member that couples the first grasping portion 4 and the second grasping portion 5, and formed in a flex shape. Therefore, a first longitudinal axis a4, which is a longitudinal direction axis of the first grasping portion 4 coupled to the distal end side of the operation potion main body 6, and a second longitudinal axis a5, which is a longitudinal direction axis of the second grasping portion 5 coupled to the proximal end side of the operation portion main body 6, are in a positional relationship intersecting with each other at the operation portion main body 6. The first longitudinal axis a4 of the first grasping portion 4 is parallel to the longitudinal axis a2 of the insertion portion.

The port rotating portion 8, which has a rotation mechanism, is rotated around the first longitudinal axis a4 of the first grasping portion 4 integrally with the insertion portion 2, to thereby be capable of changing the position of the treatment instrument insertion port 8a as shown with the dashed lines in FIG. 2, for example.

Description will be made on the operation portion main body 6 referring to FIGS. 2 to 5.

Figure 3:
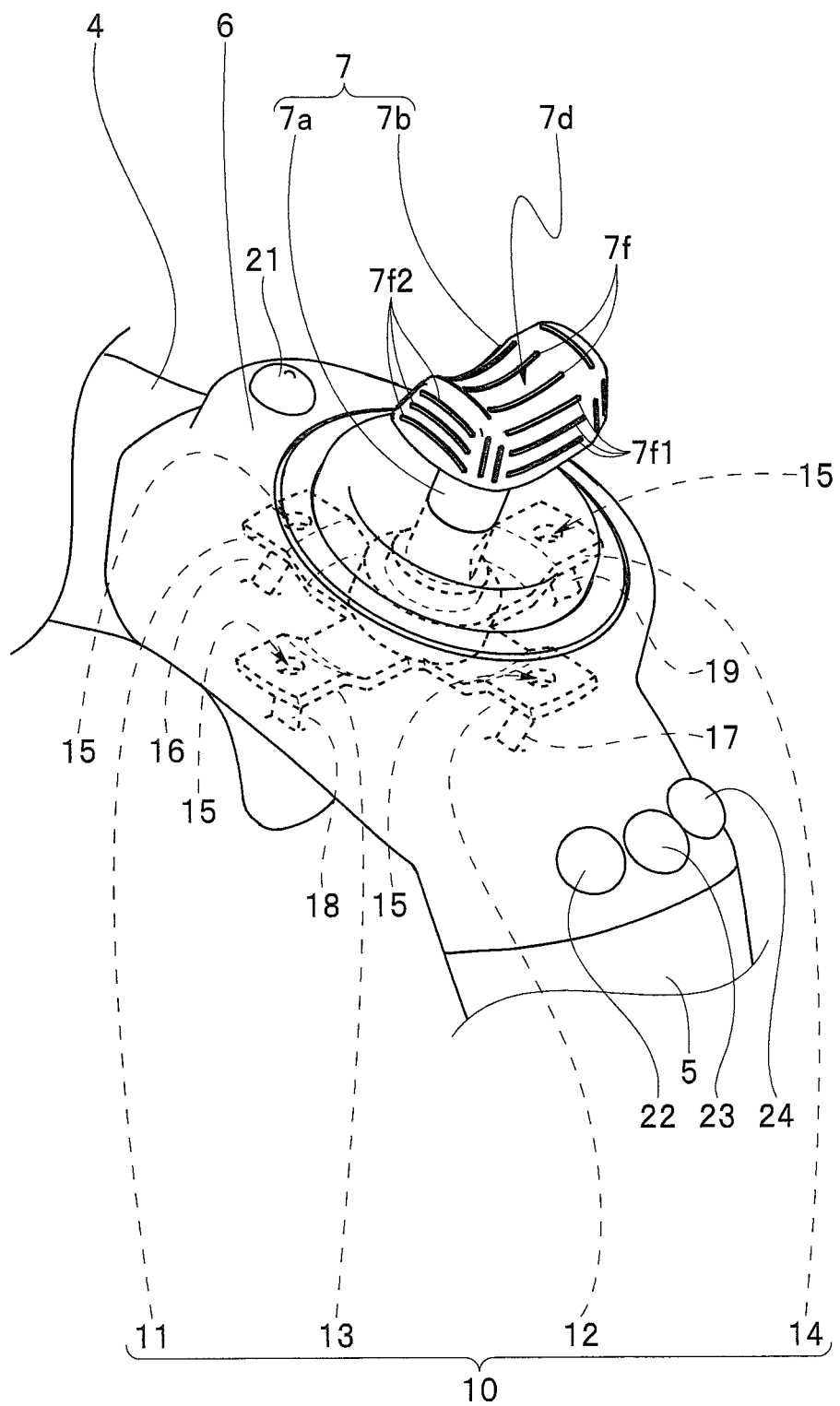
FIG. 3 mainly describes an operation portion main body and a bending operation device of an operation portion of the endoscope.

As shown in FIGS. 2 and 3, the operation portion main body 6 includes, at a middle portion thereof, a pedestal portion 6a, and a finger rest projection portion 6b. The finger rest projection portion 6b is a projection portion protruded from the flex-shaped inner side surface. On the other hand, the pedestal portion 6a is a table-like portion formed so as to protrude from the flex-shaped outer side surface which is the opposite side of the finger rest projection portion 6b.

The reference sign 7 denotes a bending operation device. A shaft member 7a, which is a bending operation lever constituting the bending operation device 7, is provided so as to stand substantially upright with respect to the upper surface 6u of the pedestal portion 6a. A cover member 6c is provided on the upper surface 6u of the pedestal portion 6a. The cover member 6c is an elastic member, and watertightly covers an opening (not shown), which is formed on the upper surface 6u and which leads to the internal space of the operation portion main body.

The substantial center of the cover member 6c covering the opening is formed so as to cover up to the middle portion of the shaft member 7a.

A finger contact portion 7b is fixed to the one end portion of the shaft member 7a, which protrudes outward from the cover member 6c. The shaft member 7a is held by the cover member 6c so as to stand upright and configured to be tillable against the elastic force of the cover member 6c.

The other end portion of the shaft member 7a is arranged in the internal space of the operation potion main body, and coupled and fixed to a suspended frame 10, which is shown with the dashed lines in FIG. 3, provided in the internal space of the operation portion main body and constituting the bending operation mechanism.

The suspended frame 10 is formed in a cross shape with four arm portions 11, 12, 13, and 14, for example. A wire fixing hole 15 is formed at a predetermined position of each of the arm portions 11, 12, 13, and 14.

The proximal-end-side end portions of bending wires 16, 17, 18, and 19 which respectively correspond to up, down, left, and right are fixed respectively to the wire fixing holes 15. The distal-end-side end portions of the bending wires 16, 17, 18, and 19 are fixed to the parts corresponding respectively to up, down, left, and right of the distal end bending piece that configures the bending portion 2b.

The bending portion 2b is configured to bend by any of the bending wires 16, 17, 18, and 19 being pulled or relaxed by the suspended frame 10 being swung in accordance with the tilting operation of the shaft member 7a.

Figure 4:
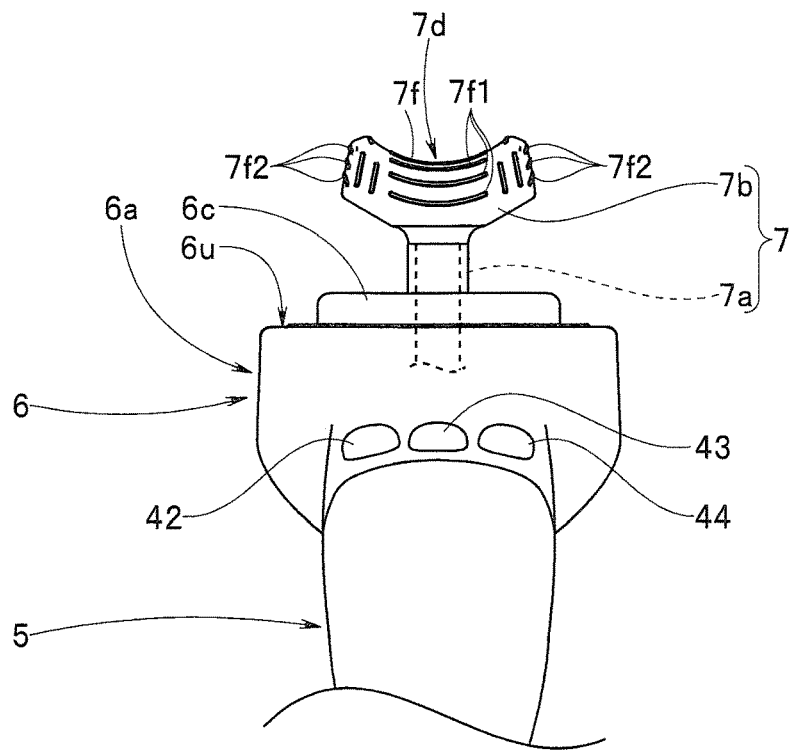
FIG. 4 describes the operation portion viewed from the direction of the arrow Y4 in FIG. 2.

As shown in FIGS. 3 and 4, the finger contact portion 7b is a hexahedron, and what is called, a substantially rectangular parallelepiped shape, or a truncated quadrangular pyramid shape formed by cutting, in parallel to the bottom surface, the apex portion side of the quadrangular pyramid. The center of the bottom surface of the finger contact portion 7b is an attaching surface to which the one end portion of the shaft member 7a is fixed. In such a fixed state, the finger contact portion 7b is arranged such that the longitudinal axis thereof is perpendicular to the first longitudinal axis a4 of the operation portion main body 6, as shown in FIG. 5.

Figure 5:
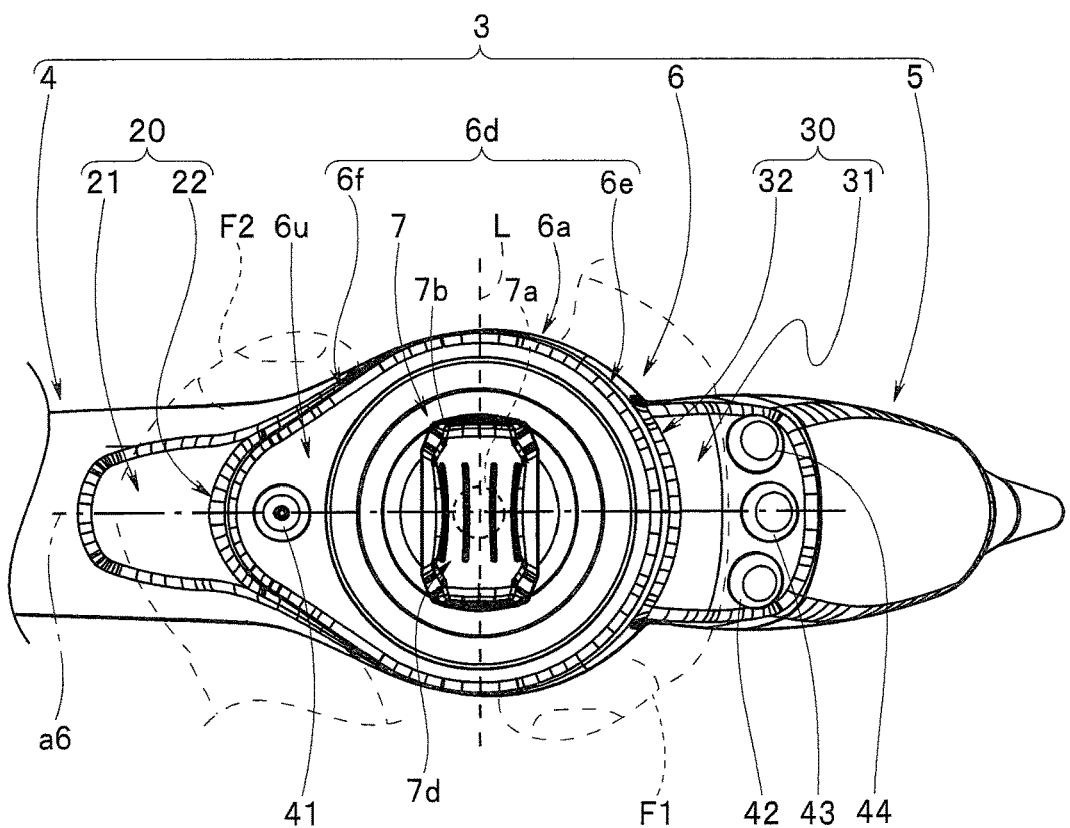
FIG. 5 describes the operation portion viewed from the direction of the arrow Y5 in FIG. 2.

As shown in FIGS. 3 to 5, a finger placing portion 7d is provided on the top surface of the finger contact portion 7b.

As shown in FIG. 5, the finger of the hand grasping the first grasping portion 4 or the finger of the hand grasping the second grasping portion 5 is placed on the finger placing portion 7d. As shown in FIG. 4, the finger placing portion 7d is a substantially U-shaped recessed portion and is a curved surface, the center of which in the longitudinal direction is recessed most.

When the operator performs bending operation of the bending portion 2b, if the operator places the finger in the finger placing portion 7d as a recessed portion to move the finger contact portion 7b in the longitudinal direction of the finger contact portion 7b, to thereby perform tilting operation of the shaft member 7a, the contact area between the finger housed in the recessed portion and the finger placing portion 7d becomes large. Therefore, it is easy for the operator to perform tilting operation of the shaft member 7a with the finger placing portion 7d, without releasing the placed finger from the finger placing portion 7d.

Figure 6:
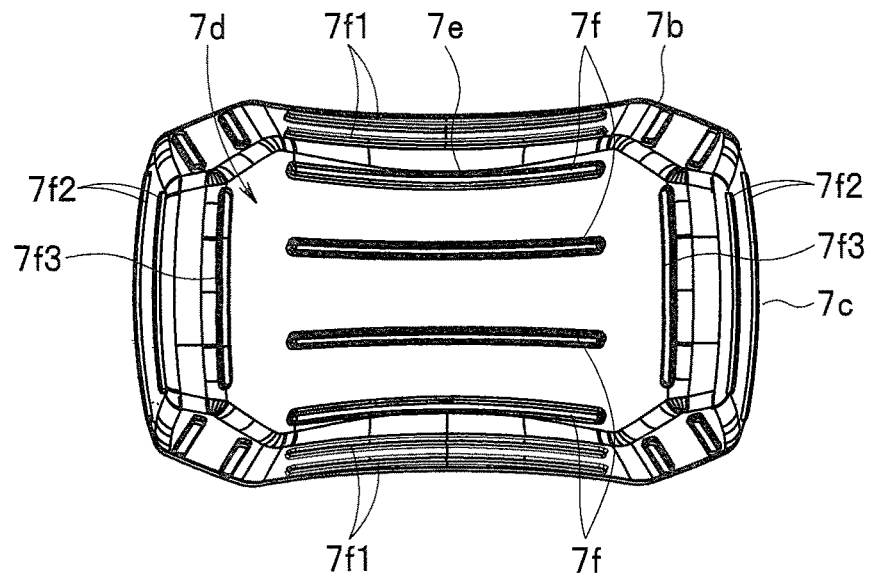
FIG. 6 is a top view of a finger contact portion viewed from the direction of the arrow Y5 in FIG. 2.

As shown in FIGS. 3, 4, and 6, a plurality of projection portions 7f that are substantially parallel to the long sides 7e are provided, as slip stoppers, on the curved surface of the finger placing portion 7d. In addition, on each of the side surfaces respectively including the long sides 7e of the finger placing portion 7d, a plurality of projection portions 7f1, which are substantially parallel to the long sides 7e, are provided as slip stoppers. Furthermore, on each of the side surfaces respectively including short sides 7c of the finger placing portion 7d, a plurality of projection portions 7f2, which are substantially parallel to the short sides 7c, are provided as slip stoppers.

As a result, as described above, when the operator places the finger in the finger placing portion 7d to move the finger contact portion 7b in the short direction perpendicular to the longitudinal direction to tilt the shaft member 7a, the fingertip and finger pulp of the finger arranged in the finger placing portion 7d touch the projection portions 7f1 and 7f, which prevents the slippage of the finger. As a result, the tilting operation becomes easier.

Note that projection portions 7f3, which are parallel to the short sides 7c, may be provided, as slip stoppers, in the vicinity of the top surface of the finger placing portion 7d as the substantially U-shaped recessed portion of the finger contact portion 7b, as shown in FIG. 6. With such a configuration, during the tilting operation for moving the finger contact portion 7b in the longitudinal direction of the finger contact portion 7b, the finger housed in the finger placing portion 7d touches the projection portions 7f3, which prevents the slippage of the finger on the finger placing portion 7d. As a result, the tilting operation becomes easier.

In addition, each of the side surfaces respectively including the long sides 7e of the finger contact portion 7b may be formed with a curved surface, the center of which in the longitudinal direction is recessed most. In this case, the projection portions 7f1, which are substantially parallel to the long sides 7e, may be provided on each of the recessed curved surface as slip stoppers.

As a result, when the operator places his or her finger on the finger placing portion 7d, the fingertip and finger pulp are placed in close contact not only with the top surface of the finger contact portion 7b but also with the recessed curved surface, which enables the operability to be increased.

Figure 7:
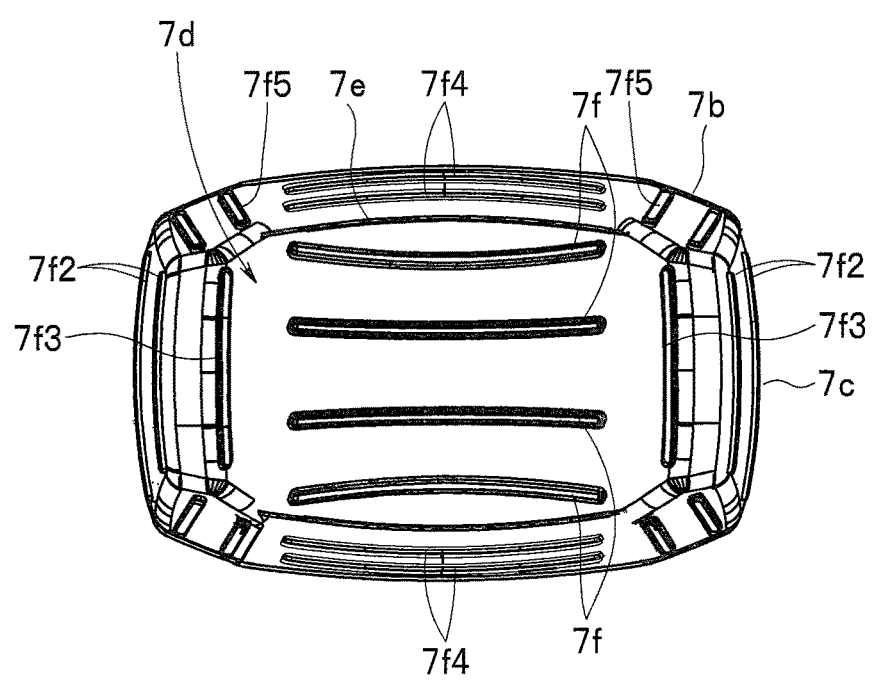
FIG. 7 describes another exemplary configuration of the finger contact portion.

Note that, in the above description, each of the side surfaces respectively including the long sides 7e of the finger contact portion 7b is formed with the curved surface, the center of which in the longitudinal direction is recessed most. However, as shown in FIG. 7, each of the side surfaces respectively including the long sides 7e of the finger contact portion 7b may be formed with a convex curved surface, the center of which in the longitudinal direction is projected most. In this case, projection portions 7f4, which are parallel to the long sides 7e, and the projection portions 7f5, which are substantially perpendicular to the long sides 7e, may be provided as slip stoppers at positions between the center of the curved surface and the vicinity of the both short sides of the side surfaces.

With such a configuration, when the operator places his or her finger on the finger placing portion 7d, the fingertip and finger pulp are placed not only on the top surface of finger contact portion but also on the projection portions 7f4, 7f5 on the convex curved surfaces, which provides favorable operability. In addition, when the operator performs tilting operation for moving the finger contact portion 7b in the longitudinal direction of the finger contact portion 7b, the finger is caught on the projection portions 7f5, to thereby prevent the finger from slipping.

As shown in FIGS. 2 and 5, the first step portion 20 and the second step portion 30 are provided on the operation portion main body 6 so as to be opposed to each other across the pedestal portion 6a.

The first step portion 20 is provided at a position which is outside of a peripheral edge 6d of the pedestal portion 6a and which is on the distal end side with respect to a distal-end-side peripheral edge 6f located on the side of the first grasping portion 4. On the other hand, the second step portion 30 is provided at a position which is outside of the peripheral edge 6d of the pedestal portion 6a and which is on the proximal end side with respect to a proximal-end-side peripheral edge 6e located on the opposite side of the first step portion 20 across the bending operation device 7.

Note that the peripheral edge 6d of the pedestal portion 6a is oval, for example, as shown in FIG. 5. The peripheral edge 6d is divided into two parts, i.e., the distal-end-side peripheral edge 6f and the proximal-end-side peripheral edge 6e across a virtual line L perpendicular to a longitudinal axis a6 of the operation portion main body 6 on the upper surface 6u and passing through the center of the shaft member 7a.

The distal-end-side peripheral edge 6f is a tapered portion formed such that the width dimension thereof becomes smaller as separating from the shaft member 7a. In contrast, the proximal-end-side peripheral edge 6e is a semicircular portion with the intersection of the virtual line L and the axis a6 as a center.

Note that the distal-end-side peripheral edge 6f may be a semicircular portion or the proximal-end-side peripheral edge 6e may be a tapered portion.

The first step portion 20 includes: the upper surface 6u of the pedestal portion 6a, which is an upper step surface; a first step surface 21, which is a lower step surface, formed with a plane or a curved surface; and a first rising surface 22. The first rising surface 22 is a pedestal portion distal-end-side side surface formed from the distal-end-side peripheral edge 6f of the pedestal portion 6a to the first step surface 21.

The second step portion 30 includes: the upper surface 6u of the pedestal portion 6a, which is an upper step surface; a second step surface 31, which is a lower step surface, fomied with a plane or a curved surface; and a second rising surface 32. The second rising surface 32 is a pedestal portion proximal-end-side side surface formed from the proximal-end-side peripheral edge 6e of the pedestal portion 6a to the second step surface 31.

Note that a third step portion similar to the first step portion 20 may be formed on a surface which is on the distal end side of the finger rest projection portion 6b and which is the opposite side of the surface on which the first step portion 20 is formed, and a fourth step portion similar to the second step portion 30 may be formed on a surface which is on the proximal end side of the finger rest projection portion 6b and which is the opposite side of the surface on which the second step portion 30 is formed.

Both the first step portion 20 and the third step portion, or only the third step portion may be formed on the distal end side of the operation portion main body 6. Furthermore, both the second step portion 30 and the fourth step portion, or only the fourth step portion may be formed on the proximal end side of the operation portion main body 6.

Note that, in the above-described embodiment, a first operation switch 41 is arranged on the upper surface 6u so as to be located on the distal end side with respect to the shaft member 7a which stands upright with respect to the upper surface 6u. In addition, a second operation switch 42, a third operation switch 43, and a fourth operation switch 44 are aligned on the proximal end side of the second step surface 31 which constitutes the second step portion 30 so as to be located at positions where the finger F1 shown by the dashed lines in FIG. 5 does not contact.

Alternatively, a plurality of operation switches may be arranged on the distal end side with respect to the upright shaft member 7a on the upper surface 6u. In addition, one or a plurality of operation switches may be arranged on the distal end side of the first step surface 21 which constitutes the first step portion 20 so as to be located at the position or positions where the finger F2 shown by the dashed lines in FIG. 5 does not contact.

Description will be made on operation portion grasping manners of the endoscope 1 which is configured as described above.

The operation portion 3 of the endoscope 1 includes the first grasping portion 4, the second grasping portion 5, and the operation portion main body 6, as described above. The operation portion main body 6 includes the pedestal portion 6a, and on the upper surface 6u of the pedestal portion 6a, the shaft member 7a constituting the bending operation device 7 is provided so as to stand substantially upright with respect to the upper surface 6u. In addition, the first step portion 20 and the second step portion 30 are provided so as to be opposed to each other across the pedestal portion 6a of the operation portion main body 6.

Therefore, the operation portion 3 of the endoscope 1 can be grasped as shown in FIGS. 8A to 9C to be described below, depending on the size of the hand or the lengths of the fingers of the operator, or the preference of the operator.

Figure 8A:
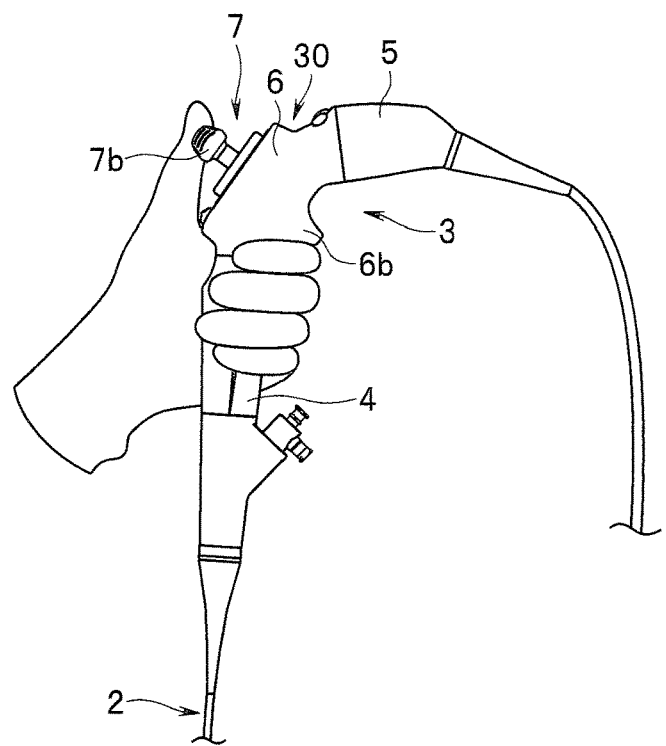
FIG. 8A illustrates a state where an operator with large hands grasps the operation portion in a first grasping manner.
Figure 8B:
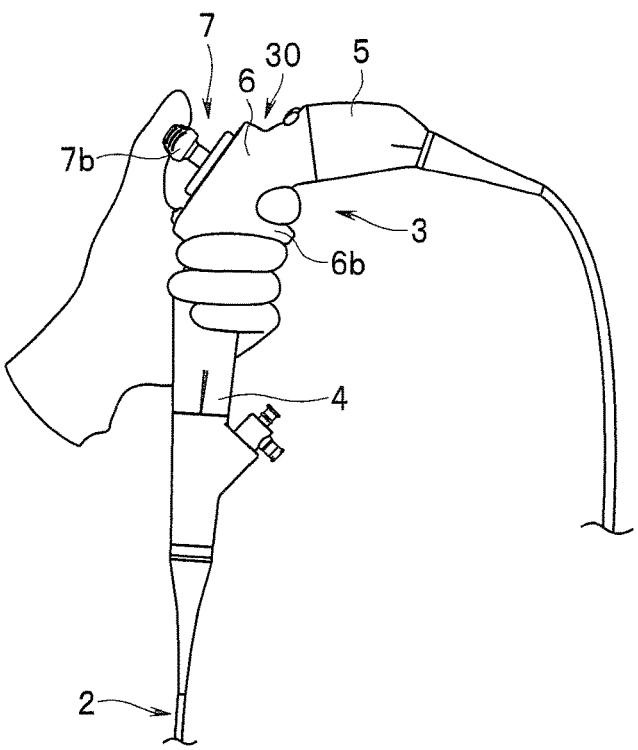
FIG. 8B illustrates a state where an operator with hands of a standard size grasps the operation portion in the first grasping manner.
Figure 8C:
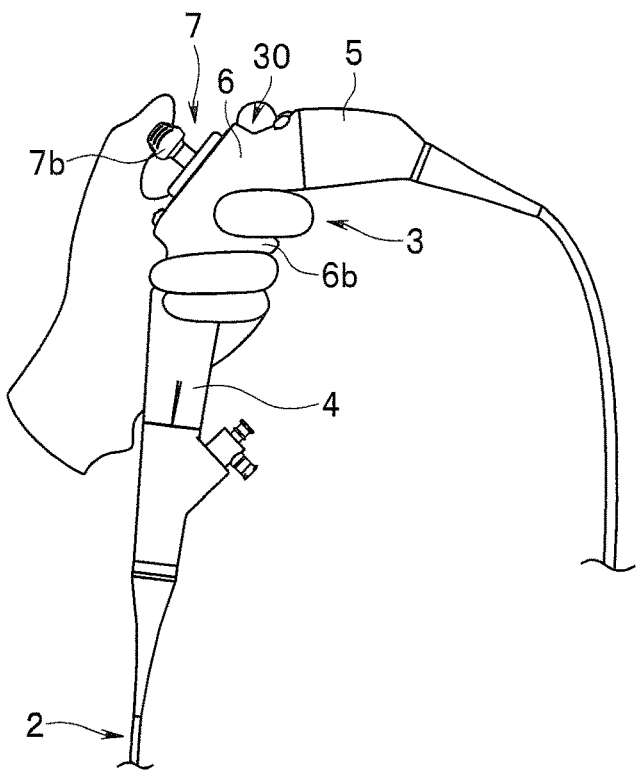
FIG. 8C illustrates a state where an operator with small hands grasps the operation portion in the first grasping manner.

FIGS. 8A to 8C illustrate the first grasping manner in which the first grasping portion 4 of the operation portion 3 is grasped with the left hand of the operator, for example. In this first grasping manner, the insertion portion 2 is brought into a state hung from the operation portion 3 along the vertical axis.

The first grasping manner shown in FIG. 8A is suitable for the operator with large hands and the operator with long fingers.

The operator with large hands or the operator with long fingers places the four fingers on the first grasping portion 4 to grasp the operation portion 3, and operate the bending operation device 7 with the thumb of the hand grasping the first grasping portion 4. Specifically, the operator places the little finger, the ring finger, the middle finger, and the forefinger of the left hand on the first grasping portion 4 which is located on the distal end side with respect to the finger rest projection portion 6b. Then, the operator places the thumb of the left hand on the finger placing portion 7d provided on the finger contact portion 7b, to perform tilting operation of the bending operation device 7.

Thus, the operator with large hands or the operator with long fingers places the four fingers appropriately on the first grasping portion 4, to be capable of grasping the operation portion 3 in the first grasping manner in a secure and stable state, and placing the thumb on the finger placing portion 7d which is a U-shaped recessed portion. As a result, the problem that the thumb falls off from the finger contact portion 7b is prevented, which enables the tilting operation of the shaft member 7a to be smoothly and securely performed.

The first grasping manner shown in FIG. 8B is suitable for an operator with hands of a standard size and fingers of standard lengths.

The operator with hands of the standard size and fingers of standard lengths places the three fingers, i.e., the little finger, the ring finger, and the middle finger of the left hand on the first grasping portion 4, and places the forefinger of the left hand on the proximal end surface side of the finger rest projection portion 6b, to grasp the operation portion 3. Then, the operator places the thumb of the left hand on the finger placing portion 7d provided on the finger contact portion 7b of the bending operation device 7, as described above.

Thus, the operator places the little finger, ring finger, and the middle finger on the first grasping portion 4, and places the forefinger on the proximal end surface side of the finger rest projection portion 6b. This enables the operator with hands of the standard size to place the hand and fingers in the vicinity of the operation portion main body 6, thereby being capable of grasping the operation portion 3 in the first grasping manner in a secure and stable state. In addition, the operator can perform the tilting operation of the shaft member 7a favorably with the thumb placed on the finger placing portion 7d, as described above.

The first grasping manner shown in FIG. 8C is suitable for an operator with small hands.

The operator with small hands places two fingers, i.e., the little finger and the ring finger of the left hand on the first grasping portion 4, places the middle finger on the proximal end surface side of the finger rest projection portion 6b, and places the forefinger of the left hand on the second step portion 30 such that the palm side of the forefinger is placed on the second rising surface 32 as shown by the dashed lines F1 in FIG. 5, to grasp the operation portion main body 6 by pinching the operation portion main body 6 with the middle finger and the forefinger, and thereby the operator grasps the operation portion 3. Then, the operator places the thumb of the left hand on the finger placing portion 7d provided on the finger contact portion 7b of the bending operation device 7, as described above.

Thus, the operator places the little finger and the ring finger on the first grasping portion 4, places the middle finger on the proximal end surface side of the operation main body 6, and places the forefinger on the second step portion 30. This enables the operator with small hands and short fingers to place the hand and fingers closer to the operation portion main body 6, to thereby be capable of grasping the operation portion 3 in the first grasping manner in a secure and stable state.

In addition, when the operator with small hands performs tilting operation of the shaft member 7a with the thumb, the operator applies, as appropriate, a pressing force in the direction opposite to the tilting operation direction from the forefinger to the proximal-end-side peripheral edge 6e. As a result, the operation portion 3 is prevented from moving or rotating in the hand grasping the operation potion 3 following the movement of the thumb with which the tilting operation is performed.

Accordingly, the force from the thumb is effectively transmitted to the shaft member 7a through the finger contact portion 7b, which enables the tiling operation with the thumb to be smoothly and securely performed.

Note that, in the descriptions of above-described FIGS. 8A to 8C, the first grasping portion 4 is grasped with the left hand. However, the first grasping portion 4 may be grasped with the right hand. In addition, the finger of the hand of the operator grasping the operation portion 3 in the first grasping manner is placed on the second step portion 30. Therefore, the second step portion 30 may be also referred to as a first grasping manner step portion.

Figure 9A:
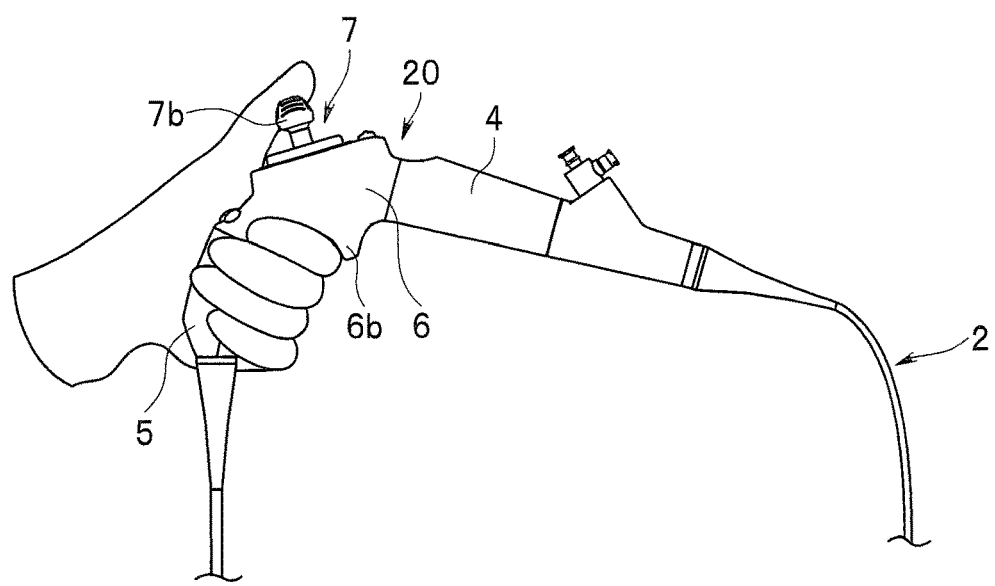
FIG. 9A illustrates a state where the operator with large hands grasps the operation portion in a second grasping manner.
Figure 9B:
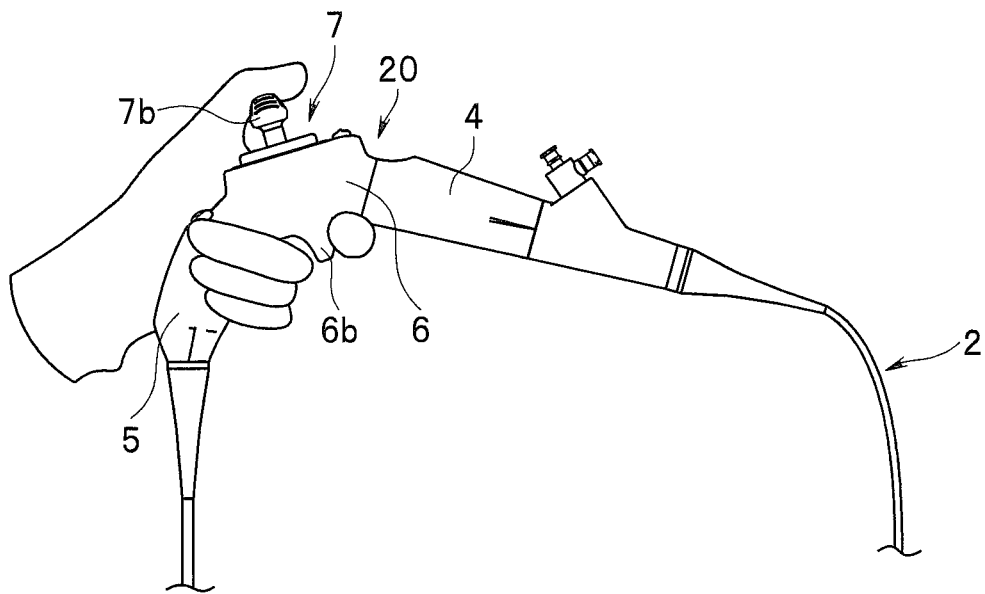
FIG. 9B illustrates a state where the operator with hands of the standard size grasps the operation portion in the second grasping manner.
Figure 9C:
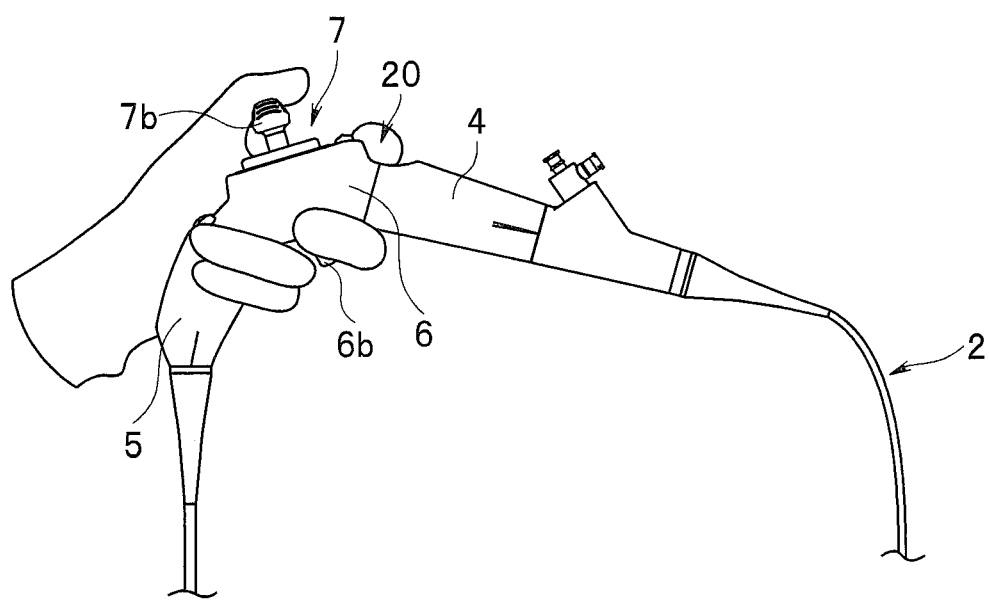
FIG. 9C illustrates a state where the operator with small hands grasps the operation portion in the second grasping manner.

Next, the second grasping manner shown in FIGS. 9A to 9C is a grasping manner in which the second grasping portion 5 of the operation portion 3 is grasped with the left hand of the operator, for example, and the longitudinal axis a2 of the insertion portion 2 extended from the operation portion main body 6 of the operation portion 3 is arranged substantially horizontally. In the second grasping manner shown in FIGS. 9A to 9C, the operation portion 3 is grasped as if the operator grips a pistol. Therefore, the second grasping manner is also referred to as pistol-gripping manner.

The second grasping manner shown in FIG. 9A is suitable for the operator with large hands and an operator with long fingers.

The operator with large hands or the operator with long fingers places the four fingers on the second grasping portion 5 to grasp the operation portion 3, and operates the bending operation device 7 with the thumb of the hand grasping the second grasping portion 5. Specifically, the operator places the little finger, the ring finger, the middle finger, and the forefinger of the left hand on the second grasping portion 5 at the positions on the proximal end with respect to the finger rest projection portion 6b, to grasp the second grasping portion 5. Then, the operator places the thumb of the left hand on the finger placing portion 7d provided on the finger contact portion 7b of the bending operation device 7, to perform tilting operation of the bending operation device 7.

Thus, the operator with large hands or the operator with long fingers appropriately places the four fingers on the second grasping portion 5, to thereby be capable of grasping the operation portion 3 in the pistol-gripping manner in the secure and stable state, and then placing the thumb on the finger placing portion 7d which is a U-shaped recessed portion. As a result, similarly as in the above-described embodiment, the problem that the thumb falls off from the finger contact portion 7b is prevented, which enables the tilting operation of the shaft member 7a to be smoothly and securely performed.

The second grasping manner shown in FIG. 9B is suitable for the operator with hands of a standard size and fingers of standard lengths.

The operator with hands of the standard size and fingers of standard lengths places the three fingers, i.e., the little finger, the ring finger, the middle finger of the left hand on the second grasping portion 5, and places the forefinger of the left hand on the distal end surface side of the finger rest projection portion 6b, to grasp the operation portion 3. Then, the operator places the thumb of the left hand on the finger placing portion 7d provided on the finger contact portion 7b of the bending operation device 7, as described above.

Thus, the operator places the little finger, the ring finger, and the middle finger on the second grasping portion 5 and places the forefinger at the finger rest projection portion 6b. This enables the operator with hands of the standard size to place the hand and fingers in the vicinity of the operation portion main body 6, to thereby be capable of grasping the operation portion 3 in the second grasping manner in the secure and stable state. In addition, as described above, the operator can perform the tilting operation of the shaft member 7a favorably with the thumb placed on the finger placing portion 7d.

The second grasping manner shown in FIG. 9C is suitable for the operator with small hands.

The operator with small hands places the two fingers, i.e., the little finger and the ring finger of the left hand on the second grasping portion 5, places the middle finger of the left hand on the distal end surface side of the finger rest projection portion 6b, and then places the forefinger of the left hand on the first step portion 20 such that the palm side of the forefinger is placed on the first rising surface 22 as shown by the dashed lines F2 in FIG. 5, to grasp the operation portion 3. Then, the operator places the thumb of the left hand on the finger placing portion 7d provided on the finger contact portion 7b of the bending operation device 7, as described above.

Thus, the operator places the little finger and the ring finger on the second grasping portion 4 and places the middle finger and the forefinger on the operation portion main body 6 to grasp the operation portion main body 6 by pinching the operation portion main body 6 with the middle finger and the forefinger, to thereby grasp the operation portion 3 in a pistol-gripping manner. This enables the operator with small hands and short fingers to place the hand and fingers closer to the operation portion main body 6, to thereby be capable of grasping the operation portion 3 in the secure and stable state.

In addition, when the operator with small hands performs tilting operation of the shaft member 7a with the thumb, the operator applies, as appropriate, a pressing force in the direction opposite to the tilting operation direction from the forefinger to the distal-end-side peripheral edge 6f. As a result, the operation portion 3 is prevented from moving or rotating in the hand grasping the operation potion 3 following the movement of the thumb with which the tilting operation is performed.

Consequently, the force form the thumb is effectively transmitted to the shaft member 7a through the finger contact portion 7b, which enables the tilting operation with the thumb to be smoothly and securely performed.

Note that, in the above-described descriptions of FIGS. 9A to 9C, the second grasping portion 5 is grasped with the left hand. However, similarly as in the grasping manner shown in FIGS. 8A to 8C, the second grasping portion 5 may be grasped with the right hand. In addition, the finger of the hand of the operator grasping the operation portion 3 in the second grasping manner is placed on the first step portion 20. Therefore, the first step portion 20 may be also referred to as a second grasping manner step portion.

In the endoscope 1 according to the embodiment described above, the operation portion 3 includes the first grasping portion 4, the second grasping portion 5, and the operation portion main body 6. However, the endoscope may be configured as illustrated in FIGS. 10 and 11.

Figure 10:
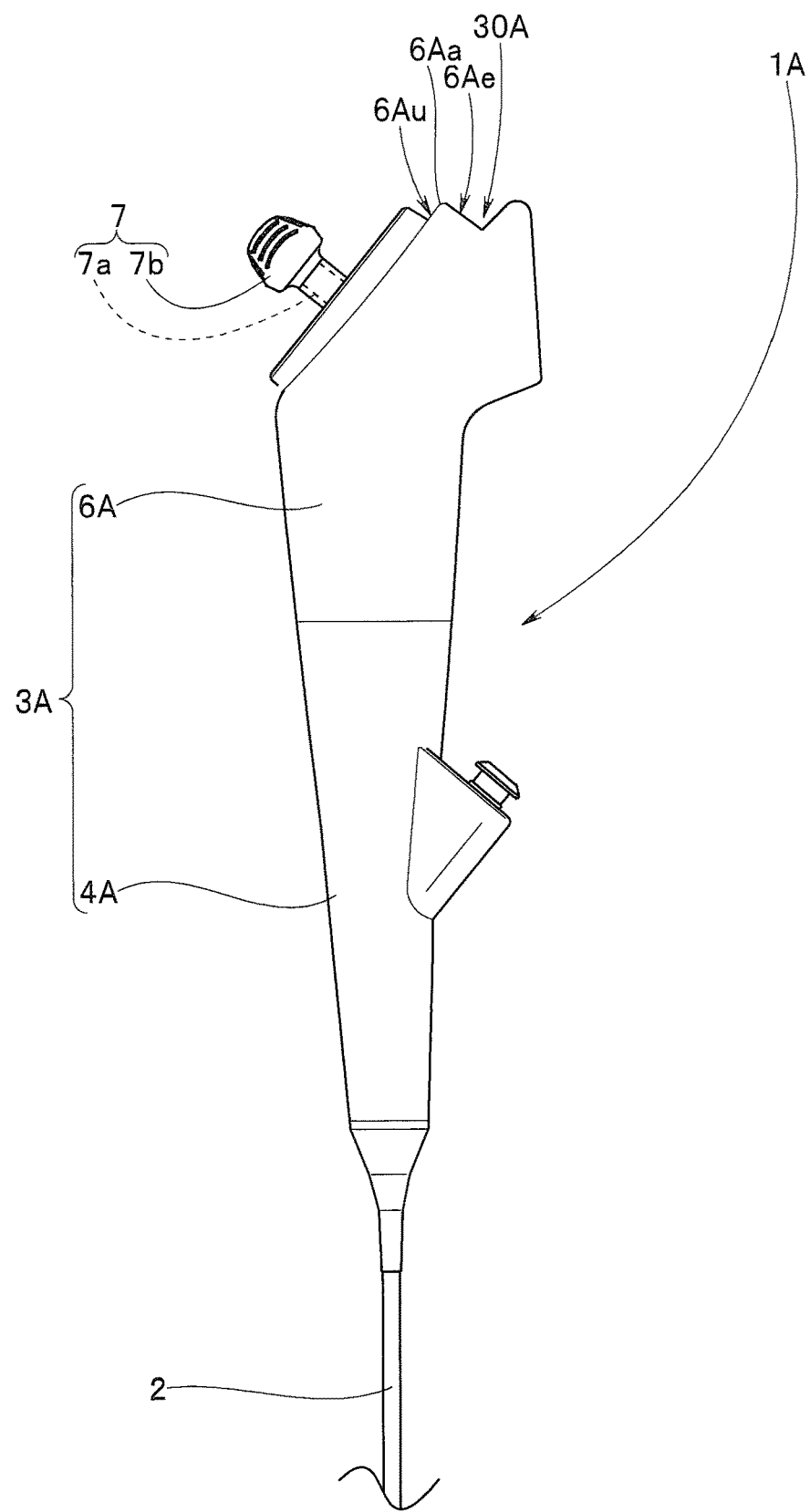
FIG. 10 describes an endoscope having another configuration in which the endoscope includes an operation portion provided with a first grasping portion and an operation portion main body.
Figure 11:
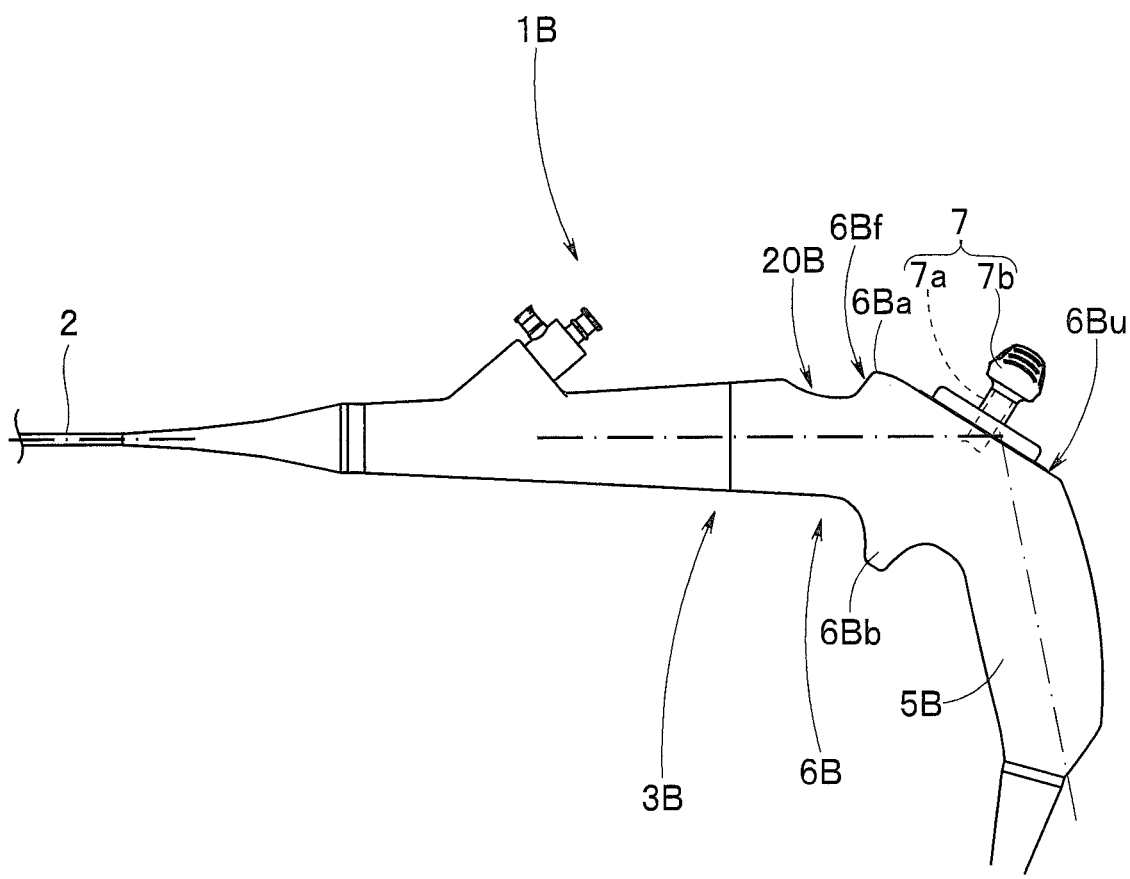
FIG. 11 describes an endoscope having yet another configuration in which the endoscope includes an operation portion provided with a second grasping portion and an operation portion main body.

As shown in FIG. 10, an endoscope 1A includes an operation portion 3A including a first grasping portion 4A and an operation portion main body 6A. The operation portion main body 6A includes a pedestal portion 6Aa. Similarly as in the above-described embodiment, the shaft member 7a constituting the bending operation device 7 is protruded from the pedestal portion 6Aa so as to stand upright with respect to an upper surface 6Au.

A first grasping manner step portion 30A is provided on the proximal end side of the operation portion main body, which is the proximal end side of the pedestal portion 6Aa and which is the opposite side of the first grasping portion 4A across the bending operation device 7.

With such a configuration, the operator places the little finger, the ring finger, and the middle finger on the first grasping portion 4A of the endoscope 1A, and places the forefinger on the first grasping manner step portion 30A, to thereby grasp the operation portion 3A. As a result, the operator grasps the operation portion 3 with the left hand, to thereby be capable of obtaining a more stable grasping state.

In addition, when performing the tilting operation of the shaft member 7a, the operator applies a pressing force in the direction opposite to the tilting operation direction from the forefinger to the proximal-end-side peripheral edge 6Ae of the pedestal portion 6Aa, to hold the operation portion 3A. This provides the same effect as that of the endoscope 1 illustrated in FIG. 8C, that is, the operation portion 3A is prevented from moving or rotating in the hand grasping the operation potion 3A following the movement of the thumb with which the tilting operation is performed.

In contrast, as shown in FIG. 11, an endoscope 1B includes an operation portion 3B including an operation portion main body 6B and a second grasping portion 5B. The operation portion 3B is provided with a pedestal portion 6Ba. Similarly as in the above-described embodiment, the shaft member 7a constituting the bending operation device 7 is protruded from the pedestal portion 6Ba so as to stand upright with respect to an upper surface 6Bu.

A second grasping manner step portion 20B is provided on the distal end side of the operation portion main body, which is outside of the peripheral edge 6Bd of the pedestal portion 6Ba and which is the opposite side of the second grasping portion 5B across the bending operation device 7.

According to such a configuration, the operator places the little finger and ring finger on the second grasping portion 5B of the endoscope 1B, places the middle finger on the distal end surface side of the finger rest projection portion 6b, and places the forefinger on the second grasping manner step portion 20B, to grasp the operation portion 3B. As a result, the operator places the hand and fingers in the vicinity of the operation portion main body 6B, to thereby be capable of grasping the operation portion 3B with the left hand in a secure and stable state.

In addition, when performing the tilting operation of the shaft member 7a, the operator applies a pressing force in the direction opposite to the tilting operation direction from the forefinger to the distal-end-side peripheral edge 6Bf of the pedestal portion 6Ba, to grasp the operation portion 3B. This provides the same effect as that of the endoscope 1 shown in FIG. 9C, that is, the operation portion 3B is prevented from moving or rotating in the hand grasping the operation potion 3B following the movement of the thumb with which the tilting operation is performed.

Note that the present invention is not limited to the above-described embodiments and the modified examples, and various modifications and changes are possible. Such modifications and changes are also within the technical range of the present invention.

The present invention is capable of providing the endoscope which is configured to be easily held by the operator, regardless of the size of the hand and lengths of the fingers of the operator or the preference of the operator, and which includes the bending operation device that enables smooth tilting operation thereof to be performed by allowing the operator to effectively transmit a force from the finger placed on the finger contact portion to the bending operation lever, irrespective of the tilting operation direction, while allowing the operator to hold the operation portion main body in the secure and stable state with the hand grasping the grasping portion.

What is claimed is:

1. An endoscope comprising:
an insertion portion which includes a bending portion and into which bending wires corresponding to four bending directions of up, down, left, and right are inserted;
an operation portion comprising:
an operation portion main body provided on a proximal end side of the insertion portion, the operation portion main body including a pedestal portion provided to protrude from the operation portion main body; and
a grasping surface provided so as to be continuous with the operation portion main body;
a bending operation lever provided so as to protrude outward from a surface of the pedestal portion, the bending operation lever being configured to be tilted by an operator with a finger of a hand grasping the grasping surface so as to pull at least one of the bending wires in a state where the operator grasps the grasping surface of the operation portion; and
a finger contact surface configured to enable the finger of the operator's hand grasping the grasping surface to be placed on the finger contact surface when the bending operation lever is tilted, the finger contact surface being provided at a distal end of the bending operation lever wherein
a step is formed on a periphery of the pedestal portion, the step being provided so as to be continuous with a side surface extending from the pedestal portion towards the step, the step being formed on an opposite side of the grasping surface grasped by the operator across the bending operation lever,
the step is formed to enable a finger of the operator's hand grasping the grasping portion, which is different from the finger placed on the finger contact portion, to be placed on the step.

2. The endoscope according to claim 1, wherein the finger contact surface includes a finger placing portion which is a U-shaped recessed portion having a curved surface, a center part of which is recessed most.

3. The endoscope according to claim 1, wherein
the grasping surface having a longitudinal axis parallel to a longitudinal axis of the insertion portion the operation portion main body being provided so as to be continuous with a proximal end side of the grasping surface, and
the step is formed on a proximal end side of the pedestal portion.

4. The endoscope according to claim 3, wherein
the step includes the side surface and a step surface formed on a proximal end side with respect to the proximal-end-side of the pedestal portion, and
a peripheral edge on the periphery of the pedestal portion is formed in a tapered portion in which a width of an edge portion close to the side surface becomes continuously smaller than a width of a central part of the pedestal portion as separating from the pedestal portion, or formed in a semicircular portion.

5. The endoscope according to claim 1, wherein
the grasping portion having a longitudinal axis intersecting with a longitudinal axis of the insertion portion, and
the step portion is formed on a distal end side with respect to a distal-end-side peripheral edge of the pedestal portion.

6. The endoscope according to claim 5, wherein
the step includes the side surface and a step surface formed on the distal end side with respect to the distal-end-side of the pedestal portion, and
a peripheral edge on the periphery of the pedestal portion is formed in a tapered portion in which a width of an edge portion close to the side surface becomes continuously smaller than a width of a central part of the pedestal portion as separating from the pedestal portion, or formed in a semicircular portion.

7. An endoscope comprising:
an insertion portion which includes a bending portion and into which bending wires corresponding to four bending directions of up, down, left, and right are inserted;
an operation portion provided on a proximal end side of the insertion portion, the operation portion comprising:
an operation portion main body including a pedestal portion provided to protrude from the operation portion main body;
a first grasping surface provided on a distal end side of the operation portion main body, the grasping surface having a first longitudinal axis parallel to a longitudinal axis of the insertion portion; and
a second grasping surface provided on a proximal end side of the operation portion main body, the second grasping portion having a second longitudinal axis intersecting with the first longitudinal axis;
a bending operation lever provided so as to protrude outward from a surface of the pedestal portion, the bending operation lever being configured to be tilted by an operator with a finger of a hand grasping one of the first grasping surface in a first grasping manner or the second grasping surface in a second grasping manner, so as to pull at least one of the bending wires; and
a finger contact surface configured to enable the finger of the operator's hand grasping one of the first and second grasping surfaces to be placed on the finger contact portion when the bending operation lever is tilted in the grasping manner or the second grasping manner, respectively, the finger contact surface being provided at a distal end of the bending operation lever; wherein a first step is formed on a proximal periphery of the pedestal portion to enable a finger of the operator's hand, which is different from the finger placed on the finger contact portion, to be placed on the first step in the first grasping manner, the first step being provided so as to be continuous with a first side surface extending from the pedestal portion towards the first step; and a second step is formed on a distal periphery of the pedestal portion to enable a finger of the operator's hand, which is different from the finger placed on the finger contact portion, to be placed on the second step in the second grasping manner, the second step being provided so as to be continuous with a second side surface extending from the pedestal portion towards the second step.

* * * * *